(12) United States Patent
Smith et al.

(10) Patent No.: US 8,465,351 B2
(45) Date of Patent: Jun. 18, 2013

(54) PNEUMATIC COOLING APPAREL SYSTEM

(75) Inventors: Michael Smith, Portland, OR (US); David Turner, Portland, OR (US)

(73) Assignee: NIKE, Inc., Beaverton, OR (US)

(*) Notice: Subject to any disclaimer, the term of this patent is extended or adjusted under 35 U.S.C. 154(b) by 387 days.

(21) Appl. No.: 12/184,236

(22) Filed: Jul. 31, 2008

(65) Prior Publication Data

US 2010/0125928 A1  May 27, 2010

Related U.S. Application Data

(63) Continuation-in-part of application No. 10/884,340, filed on Jul. 1, 2004.

(60) Provisional application No. 60/953,201, filed on Jul. 31, 2007.

(51) Int. Cl.
*A41D 1/00* (2006.01)
*A41D 13/00* (2006.01)

(52) U.S. Cl.
USPC ............... 454/370; 2/69; 165/61

(58) Field of Classification Search
USPC ............... 454/370; 2/69; 165/61
See application file for complete search history.

(56) References Cited

U.S. PATENT DOCUMENTS

| | | | |
|---|---|---|---|
| 2,657,396 A | 11/1953 | Klein | |
| 2,897,741 A * | 8/1959 | Mauch | 454/370 |
| 3,239,305 A * | 3/1966 | Potapenko | 96/57 |
| 3,242,979 A * | 3/1966 | Shlosinger | 454/370 |
| 3,468,299 A * | 9/1969 | Amato | 2/81 |
| 4,118,946 A * | 10/1978 | Tubin | 165/46 |
| 4,165,738 A | 8/1979 | Graves et al. | |
| 4,457,295 A | 7/1984 | Roehr | |
| 4,572,188 A | 2/1986 | Augustine et al. | |
| 4,660,388 A * | 4/1987 | Greene, Jr. | 454/370 |
| 4,738,119 A | 4/1988 | Zafred | |
| 5,062,424 A | 11/1991 | Hooker | |
| 5,217,408 A * | 6/1993 | Kaine | 454/370 |
| 5,245,993 A * | 9/1993 | McGrady et al. | 2/69 |
| 5,255,390 A * | 10/1993 | Gross et al. | 2/69 |
| 5,300,100 A | 4/1994 | Hickle et al. | |
| 5,300,102 A | 4/1994 | Augustine et al. | |
| 5,320,164 A * | 6/1994 | Szczesuil et al. | 165/46 |

(Continued)

FOREIGN PATENT DOCUMENTS

| | | | |
|---|---|---|---|
| DE | 3333860 A | * | 4/1984 |
| DE | 3333860 A1 | * | 4/1984 |

(Continued)

OTHER PUBLICATIONS

Mukai et al, JP04080536A, Mar. 13, 1992, English translation.*

(Continued)

*Primary Examiner* — Steven B McAllister
*Assistant Examiner* — Phillip E Decker
(74) *Attorney, Agent, or Firm* — Plumsea Law Group LLC (57) ABSTRACT

A modular air delivery system for supplying treated air to plural individuals wearing ventilation cooling garments. These garments are formed of comfortable and flexible air permeable inner layer and an air impermeable outer layer to define a plurality of air channels therebetween. In one disclosed embodiment, a flexible channel support is disposed between the inner and outer layer to prevent the layers from collapsing together during use.

18 Claims, 5 Drawing Sheets

U.S. PATENT DOCUMENTS

| | | | |
|---|---|---|---|
| 5,323,727 A * | 6/1994 | Heaton | 114/315 |
| 5,386,823 A | 2/1995 | Chen | |
| 5,438,707 A * | 8/1995 | Horn | 2/69 |
| 5,640,728 A | 6/1997 | Graebe | |
| 5,658,325 A | 8/1997 | Augustine | |
| 5,755,275 A * | 5/1998 | Rose et al. | 165/46 |
| 5,823,200 A | 10/1998 | Persaud | |
| 5,860,292 A | 1/1999 | Augustine et al. | |
| 5,970,519 A | 10/1999 | Weber | |
| 5,989,285 A | 11/1999 | DeVilbis et al. | |
| 6,102,936 A | 8/2000 | Augustine et al. | |
| 6,131,645 A * | 10/2000 | Barr | 454/903 |
| 6,245,096 B1 | 6/2001 | Tomic-Edgar et al. | |
| 6,254,613 B1 | 7/2001 | Harrison | |
| 6,260,201 B1 * | 7/2001 | Rankin | 2/69 |
| 6,371,976 B1 | 4/2002 | Vrzalik et al. | |
| 6,571,574 B1 * | 6/2003 | Blackstone | 62/420 |
| 6,596,019 B2 | 7/2003 | Turner | |
| 6,915,641 B2 * | 7/2005 | Harvie | 62/3.5 |
| 6,942,015 B1 * | 9/2005 | Jenkins | 165/46 |
| 6,993,930 B2 * | 2/2006 | Blackstone | 62/421 |
| 7,117,687 B2 * | 10/2006 | Naaman | 62/259.3 |
| 7,527,612 B1 * | 5/2009 | Carpenter et al. | 62/269 |
| 7,681,249 B2 * | 3/2010 | Oliver et al. | 2/102 |
| 7,698,905 B1 * | 4/2010 | Carpenter et al. | 62/259.3 |
| 7,716,940 B2 * | 5/2010 | Farnworth et al. | 62/259.3 |
| 2001/0000849 A1 * | 5/2001 | Siman-Tov et al. | 62/259.3 |
| 2004/0079517 A1 * | 4/2004 | Bueley et al. | 165/46 |
| 2004/0168459 A1 * | 9/2004 | Blackstone | 2/171.3 |
| 2005/0101911 A1 * | 5/2005 | Chester et al. | 604/113 |
| 2005/0172655 A1 * | 8/2005 | Naaman | 62/259.3 |
| 2006/0026743 A1 * | 2/2006 | Farnworth et al. | 2/455 |
| 2006/0174392 A1 * | 8/2006 | Farnworth et al. | 2/102 |
| 2009/0062892 A1 * | 3/2009 | Ilcheva et al. | 607/108 |

FOREIGN PATENT DOCUMENTS

| | | | |
|---|---|---|---|
| DE | 3333860 A1 * | 4/1984 | |
| GB | 2352959 A * | 2/2001 | |
| GB | 2352959 A * | 2/2001 | |
| JP | 4-80536 A * | 3/1992 | |
| JP | 04080536 A * | 3/1992 | |
| JP | 04209809 A * | 7/1992 | |
| JP | 2002-242007 A * | 2/2001 | |
| JP | 2002-242007 A * | 8/2002 | |
| JP | 2002242007 A * | 8/2002 | |

OTHER PUBLICATIONS

Office Action dated Jun. 29, 2005, U.S. Appl. No. 10/884,340, filed Jul. 1, 2004.

Final Office Action dated Dec. 22, 2005, U.S. Appl. No. 10/884,340, filed Jul. 1, 2004.

Office action mailed Apr. 24, 2013 in U.S. Appl. No. 10/884,340, filed Jul. 1, 2004.

* cited by examiner

PNEUMATIC COOLING APPAREL SYSTEM

CROSS-REFERENCE TO RELATED APPLICATIONS

This application is a continuation-in-part of U.S. patent application Ser. No. 10/884,340, filed on Jul. 1, 2004, which is currently pending. This application also claims priority to U.S. provisional patent application Ser. No. 60/953,201, filed on Jul. 31, 2007.

FIELD OF THE INVENTION

The present invention relates to pneumatic cooling apparel that is connected to a pneumatic aid delivery system to regulate body temperature of the apparel wearer.

BACKGROUND

Many people wear equipment and clothing designed to protect them from temperature extremes, and to regulate the temperature of their body. Professionals such as firefighters and athletes most often use this type of protective equipment and clothing, although use of such clothing is by no means limited to these users. For example, firefighters are required to wear heavy clothing that provides protection from extreme heat. While the heavy clothing worn by firefighters serves an important function by shielding the user from heat, it similarly is very warm and can lead to the wearer becoming overheated. Likewise, athletes such as football and hockey players, and racecar drivers wear heavy protective gear that provides essential protection, but which may lead to overheating. This is especially true with football players who often play in hot, humid conditions. Just as heavy protective clothing and equipment serves a necessary purpose, in doing so it can contribute to overheating, which in extreme cases may be a dangerous condition.

Various ventilation systems worn by athletes and the like have been designed for alleviating overheating caused by protective clothing and equipment. For example, U.S. Pat. Nos. 4,738,119 to Zafred, 5,970,519 to Weber, and 6,596,019 to Turner et al. each describe ventilation systems that are worn by individuals who can benefit by keeping body temperature regulated. Each of the cooling apparel systems described in these patents requires a source of a fluid that may be supplied to the apparel system. In the '119 patent the apparel device is connected to a source of liquid carbon dioxide. The cooling garment is charged with liquid carbon dioxide, which converts to a solid phase in the garment, and the garment is then disconnected from the carbon dioxide source. The solid carbon dioxide in the garment sublimates while the garment is worn to thereby cool the user. The '519 patent provides a method for connecting the garment to a source of relatively dry air—the air flows through an air permeable layer in the garment to cool the wearer. Air may be supplied to the garment from a pressurized canister mounted to a wearer's belt, a remote supply such as a compressor, or a portable blower. The '019 patent describes a ventilation system having an air bladder that receives air from a compressor to supply warm or cooled air to the ventilation system.

There is a need for improved air delivery systems designed for use with ventilation systems worn by individuals to regulate body temperature.

BRIEF SUMMARY OF THE INVENTION

The present invention provides a modular air delivery system for use in supplying treated air to plural individuals wearing ventilation apparatus. The system is modular and easily transported to any location.

Cooling air is delivered to individuals wearing cooling garments. These garments are formed of comfortable and flexible air permeable fabric inner layer and an air impermeable fabric outer layer to define a plurality of air channels therebetween. In one disclosed embodiment, a channel support is disposed between the inner and outer layer to prevent the layers from collapsing together during use of the garment.

BRIEF DESCRIPTION OF THE DRAWINGS

The invention will be better understood and its numerous objects and advantages will be apparent by reference to the following detailed description of the invention when taken in conjunction with the following drawings.

DETAILED DESCRIPTION OF THE PREFERRED EMBODIMENTS

Where ventilation systems such as those described herein are used, there is often a need to supply air to more than one user of the system. For example, many members of a football team's offense may be wearing ventilation systems such as that described below with reference to FIGS. 1 through 8 or FIGS. 9-12. Each individual player in this case needs to have a separate supply of air. The same is true of firefighters: there are instances where many individuals need to attach their ventilation system to a supply of cooling air. In addition, in many locations where ventilation systems are worn, there are a variety of restrictions in place on the types of equipment that are allowed. As just one example, many football stadiums place restrictions on the type and size of compressors that are allowed onto the sidelines—gas-powered compressors may not allowed, or if they are allowed, they must be remotely located from the place where the players need them. The same is true in ice arenas where hockey is played. The air delivery apparatus 10 described herein may be used to deliver treated air to any suitable ventilation system, and is capable of delivering treated air to plural users. One suitable ventilation system is described herein with reference to two different embodiments of ventilation garments.

Figure 1:
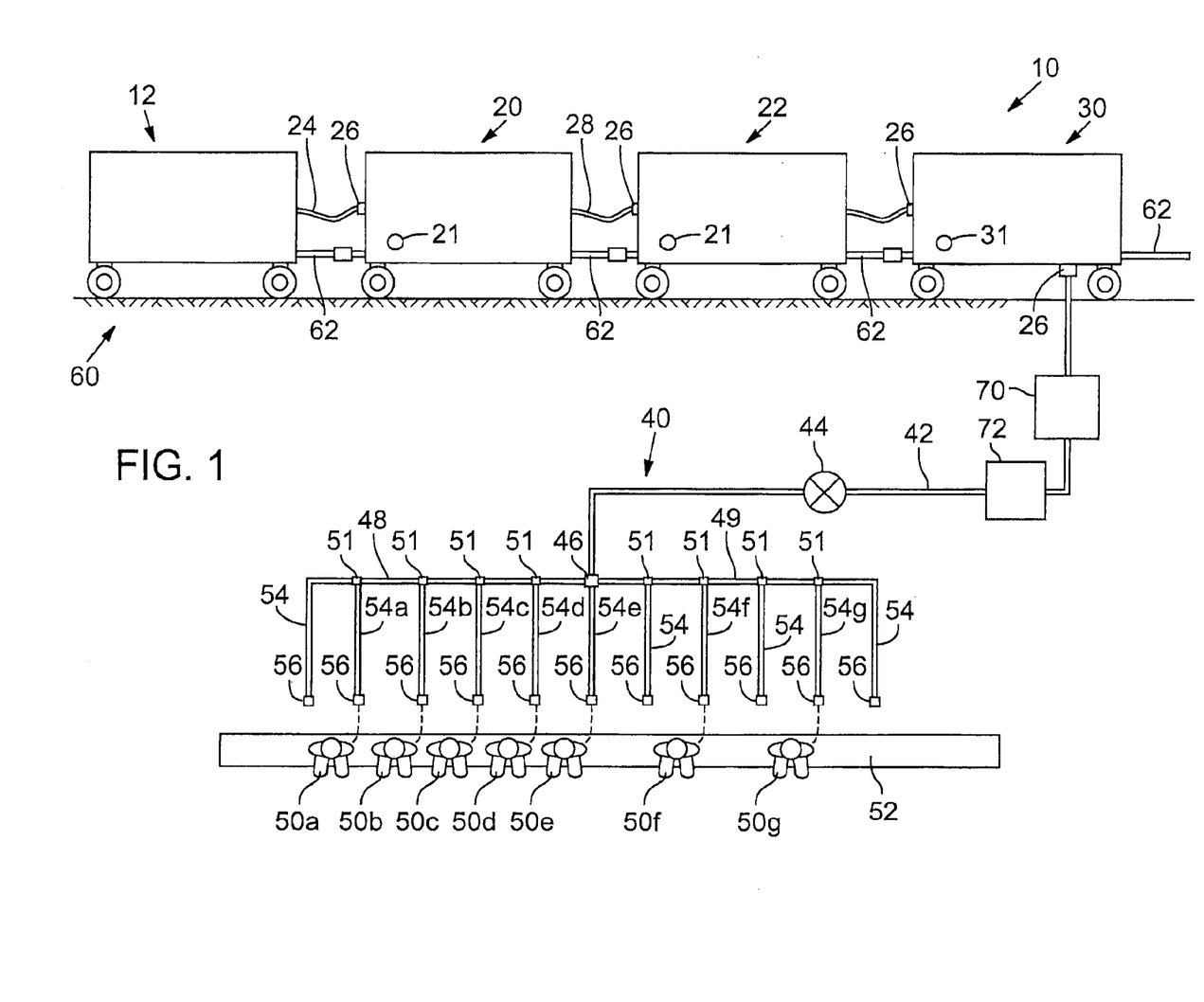
FIG. 1 is schematic view of a modular air delivery apparatus according to the present invention showing components of the apparatus and one environment in which the modular air delivery apparatus may be used.

With reference now to FIG. 1, the air delivery apparatus 10 according to the present invention is shown as including several component parts, each of which is a contained in a separate wheeled module. Thus, apparatus 10 includes an air compressor 12, a first air reservoir 20, a second, optional air reservoir 22, a dryer 30, and a treated air distribution module referenced generally with number 40 that is configured to simultaneously deliver treated air to plural ventilation systems, each worn by a wearer such as 50a, 50b, 50c... through 50g. In the illustration of FIG. 1, wearers 50 are shown to be athletes such as football players seated on a player bench 52 such as would be found on the sidelines in a football stadium. From the description that follows it will be appreciated that the number of individual connections to wearers 50 that air delivery module 40 is designed to serve may be tailored according to need. In the case of a football team, the number of wearers could be 11 as shown in FIG. 1—the number of players on the offensive and defensive teams. The invention is not limited to use by football players or players in any other sport, or any number of wearers.

Each of the components will now be separately described.

Compressor 12, each air reservoir 20, 22, and air dryer 30 are modular units that are supplied on wheeled frames 60 that allow the units to be very portable and thus easily moved from place to place without the assistance of tractors and the like. The modular units may be quickly connected to and uncoupled from one another as shown in FIG. 1 with coupling arms 62, and the coupling arms may be used as handles to push and pull the units, as with coupling arm 62 on air dryer 30. The wheeled frames 60 allow the modular units to be moved individually or together as an interconnected group as in FIG. 1. The compressor, reservoirs and air dryer may be mounted onto wheeled frames in any appropriate manner that allows the frames and the equipment mounted on them to be easily moved from location to location. While the wheeled frames make transporting the individual modular units from place to place, the modular units may be provided without wheels so long as the units are portable.

Turning now to a description of the individual modules, air compressor 12 is an electric compressor that preferably is operable on a 110V power supply, although a compressor operable on a 220V or other power supply will suffice. The preferred compressor 12 is a rotary vane type of compressor. Such compressors are available from numerous commercial suppliers. The air compressor 12 selected for use in any particular air delivery apparatus 10 should be of an appropriate size for that particular apparatus, and should have sufficient operating capacity to pressurize and maintain each air reservoir used in the apparatus. Although not shown in the drawings, air compressor 12 includes appropriate control mechanisms and operations indicators such as output air pressure and the like.

Any number of air reservoirs such as first air reservoir 20 and second air reservoir 22 may be used in series as shown in FIG. 1, and the air compressor 12 should be of sufficient size to charge each air reservoir to the desired operating pressure. In the preferred embodiment the air reservoirs 20 and 22 are pressurized to an operating pressure of about 100 lb/in$^2$ or above. Increasing the number of reservoirs 20 in an air delivery apparatus 10 increases the output capacity of the system. The air compressor 12 is connected to the first air reservoir 20 with a flexible high-pressure hose 24 that preferably is fitted with a quick-connect type of coupler 26 that allows the hose to be quickly connected to and disconnected from the air reservoir. Although a coupler 26 is shown on only the downstream end of high-pressure hose 24, each end of the hose may be fitted with a like coupler. Preferably, each high-pressure hose used in apparatus 10 will be insulated to minimize any change in air temperature resulting from environmental exposure. Moreover, the length of hosing is preferably minimized to reduce fluctuation in air temperature between modular units such as air compressor 12, and air reservoir 20. Each air reservoir 20, 22 preferably includes an air pressure gauge 21 and other appropriate control apparatus such as air pressure regulation valves and the like.

Each successive air reservoir is likewise coupled to the previous reservoir with a high-pressure hose fitted with quick-connect couplers. Thus, second air reservoir 22 is connected to first air reservoir 20 with high-pressure hose 28 equipped with coupler 26.

Air dryer 30 is a compressed air dryer having a capacity matched to the capacity of the rest of apparatus 10, and preferably is of the type having an easily replaceable, modular desiccant cartridge. The compressed air dryer 30 dries the air to a relative humidity at the outlet of the dryer that is appropriate under the conditions, considering for example the relative humidity and temperature of the ambient air, the purpose for which the air is being used, etc. In a typical example of use of apparatus 10 with a football team in typical weather conditions, air dryer 30 preferably dries the air to a relative humidity at the outlet of the dryer to a humidity in the range of between about 50% to less than 1%. It will be appreciated that the relative humidity of air leaving the dryer may vary significantly. As with the high-pressure hoses that interconnect the first and second air reservoirs, compressed air dryer 30 is coupled to second air reservoir 22 with a flexible high-pressure hose, preferably including quick connect couplers 26. Compressed air dryer 30 preferably is equipped with monitoring and control systems such as a relative humidity meter 31 that provides information about the moisture content of output air. Although not shown in the drawings, an output air pressure regulating valve may optionally be used on the output fitting from air dryer 30. In some instances the air dryer 30 may be omitted—for example, in locations where the ambient air is at a low relative humidity.

Desiccated air is output from compressed air dryer 30 to air delivery module 40, which includes a flexible, insulated high-pressure main air hose 42 that may optionally include an in-line pressure control valve 44 operable to increase and or decrease air pressure in main air hose 42 according to need. Main air hose 42 terminates in a T-fitting 46 that supplies first branch hose 48 and second branch hose 49. Each branch hose 48, 49 is fitted with plural T-fittings 51, each of which is connected to an air connection hose 54 that is used to couple the air delivery module 40 to individual wearers 50. In FIG. 1, seven individual wearers 50 are shown having their air ventilation apparel systems connected to one of the air connection hoses 54. Each air connection hose 54 has a quick connect coupler 56 on its terminal end. Quick connect couplers 56 are connectable to the input fittings on the air ventilation apparel and are one-way valve fittings that are open when a connection to an air ventilation garment is made, and closed when the connection to the garment is disconnected.

Because the air delivery apparatus 10 described above is comprised of modular units that may be quickly and easily interconnected, the entire apparatus 10 may be delivered to locations where it is needed very quickly. Because the air compressor 12 is powered by electricity, there are few restrictions on transporting the unit on most carriers such as airlines, which often restrict transportation of equipment powered with fossil fuels. The individual components of apparatus 10 may thus be transported to any location, wheeled to a specific location where wearers 50 are located (either before or after the individual modules 12, 22, etc. are connected to one another), and operated.

Figure 2:
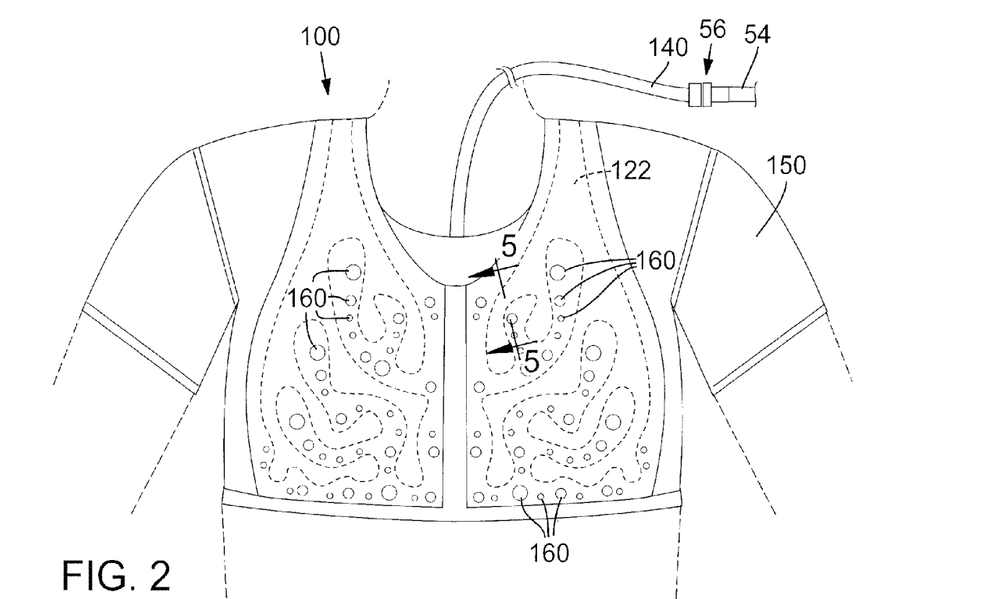
FIG. 2 is front view of a first preferred embodiment ventilation system, in this case a ventilation garment, with which the modular air delivery apparatus may be used.
Figure 3:
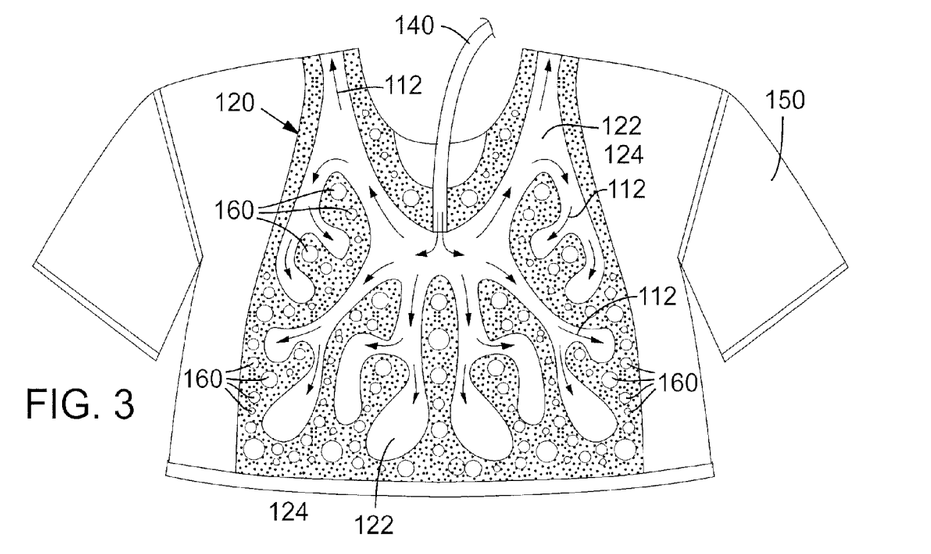
FIG. 3 is a rear view of the ventilation system shown in FIG. 2 with the outer layer of the garment removed to expose the underlying layer.
Figure 4:
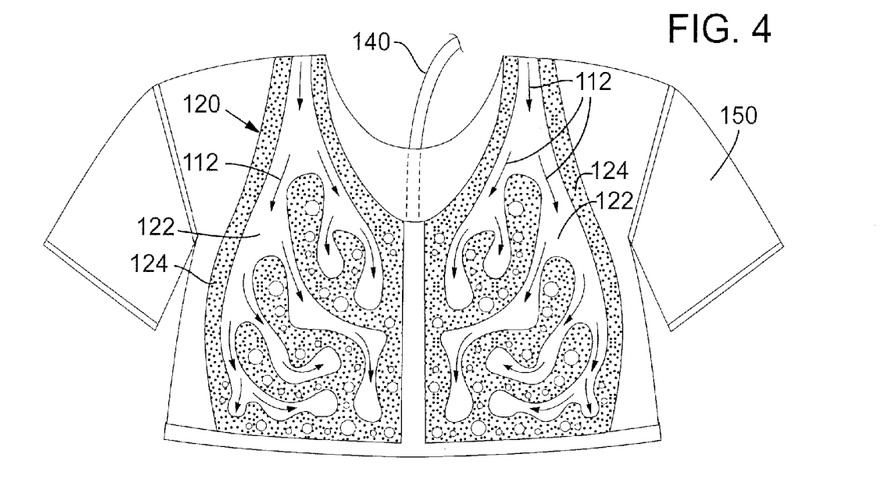
FIG. 4 is a front view of the ventilation system shown in FIG. 3, with the outer layer of the garment removed to expose the underlying layer.

Turning now to FIGS. 2 through 8, a first preferred ventilation system 100 is disclosed. The ventilation system 100 with which the air delivery apparatus 10 described above may be used is described. Although the ventilation system 100 described herein and shown in FIGS. 2 through 4 is embodied in a garment such as a T-shirt 150, it is to be understood that the ventilation system may also be incorporated with or in other items such as, for example, football helmets, firefighter's headgear, pants, jackets, sports equipment, shoes, gloves, blankets, and any other item that may be used by an individual to modify or regulate the individual's body temperature.

Figure 6:
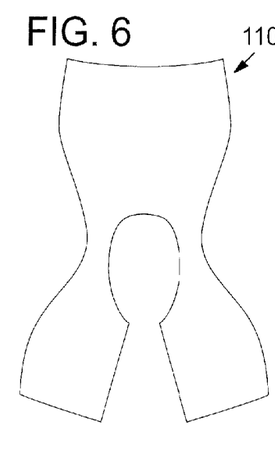
FIG. 6 is a plan view of a preferred embodiment of the inner layer of the ventilation system shown in FIG. 2, prior to the ventilation system being incorporated into a garment.
Figures 7, 8:
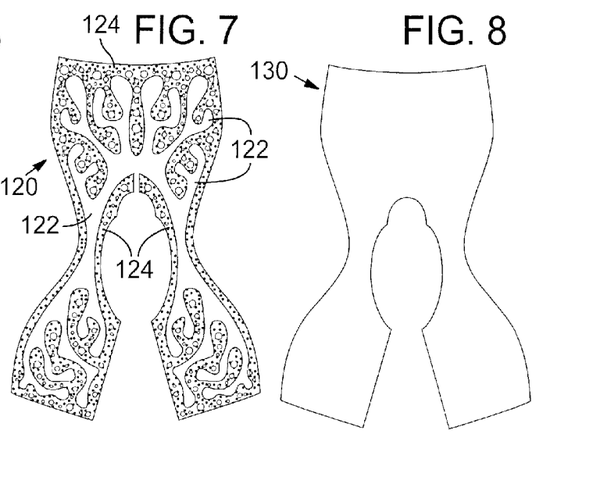
FIG. 7 is a plan view of the ventilation system shown in FIG. 6, illustrating air channels.
FIG. 8 is a plan view outer layer of the ventilation system shown in FIG. 2, prior to the ventilation system being incorporated into a garment.

With reference to FIGS. 6 through 8, a ventilation system that is designed for incorporation into a T-shirt (as shown in FIGS. 2 through 4) includes an inner layer 110 (FIG. 6), an outer layer 130 (FIG. 8) and an intermediate layer 120 (FIG. 7). Inner layer 110 is preferably a fabric material having microporous structure that has holes of a size that allows air to diffuse through the layer. Outer layer 130 is preferably a fabric material that is impermeable to air, such as fabric coated with a plastic material. The three layers 110, 120 and 130 are sandwiched together atop one another such that the intermediate layer 120 defines a series of air channels 122. The air channels 122 are operatively connected through an air hose 140 to a source of air, such as the air delivery apparatus 10 described herein.

It will be appreciated that intermediate layer 120 and the air channels 122 defined in ventilation system 100 may be formed with glue applied between the inner and outer layers 110 and 130, or may be formed by welding the inner and outer layers, 110 and 130, together, such as with radio frequency welding. As such, intermediate layer 120 need not be a distinct layer, but instead is the joined interface area between the inner and outer layers, 110 and 130, that define the air channels through the ventilation system. As noted above, the ventilation system is typically incorporated into a garment such as the T-shirt 150 shown in FIGS. 2 through 4.

Figure 5:
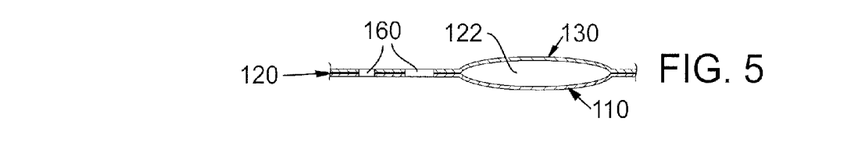
FIG. 5 is a cross sectional view taken along the line 5-5 of FIG. 2.

The portion in which the intermediate layer 120 comprises glue or welded areas is shown in the drawings with stippling and is identified in FIG. 7 with reference number 124. The arrows 112 in the drawings illustrate the flow of air through ventilation system 100. Air is introduced to ventilation system 100 through air hose 140 and flows through channels 122. When the ventilation system is incorporated into a T-shirt 150, the air channels 122 extend over the front and back portions of the garment so that air flows over the user's back, shoulders and chest. Referring to FIG. 5, air flowing through channel 122 diffuses through inner layer 120, which as noted is permeable to air, toward the wearer's body. Outer layer 130 is not air-permeable, so air flows in a one-way direction through inner layer 110, toward the wearer's body. Because outer layer 130 is not permeable, a series of through holes 160 are formed through the ventilation system 100 in the glued areas 124 to allow sweat to escape from the wearer's body to the atmosphere.

In operation, each of the individual modular units in apparatus 10 is positioned as desired and interconnected to one another as shown in FIG. 1. Air compressor 12 is connected to an appropriate power source and each air reservoir 20, 22 is charged to a predetermined operating pressure. The operating pressure is adjusted with pressure regulation control valves. Pressure control valve 44, if used, is adjusted to the desired output pressure according to the working pressure that is most suited to the type of air ventilation garment that the wearers are using. The air dryer 30 is adjusted so that the air delivered to users is desiccated relative to atmospheric air, and as noted, the relative humidity of the air delivered to users is about 30% or less.

The wearers may then connect their ventilation garments such as ventilation a systems 100 to air delivery hoses with quick connect couplers 56 as desired. Once a connection is made, air having desired moisture content and pressure is delivered to the ventilation garment.

It will be appreciated that compressed air is normally cooler than ambient air temperatures. As such, air delivery apparatus 10 need not include refrigeration systems to deliver air that is relatively cooler than ambient air. Moreover, because the air delivered from air delivery apparatus 10 to the wearers 50 has a relative humidity that is lower than that of the atmosphere, evaporative drying and the cooling effect of it is increased. Nonetheless, air delivery apparatus 10 may optionally include an air refrigerator 70 inline in the system, shown schematically in FIG. 1 in main air hose 42.

Likewise, air delivery apparatus 10 may optionally be used to deliver heated air to wearers 50 by use of an air heater 72, also shown schematically inline in main air hose 42. Where an air refrigerator 70 and/or an air heater 72 are used, the equipment is provided on a wheeled frame with quick connect couplings.

As noted above, because each of the modular units that are used in air delivery apparatus 10 are separately contained on wheeled frames (i.e., air compressor 12, air reservoir 20, air dryer 30), the entire system may be quickly transported to the precise location where it is needed. For example, in the case where athletes such as football players are wearing the ventilation systems 100, the air delivery apparatus 10 may be set up next to the players' bench. Hockey teams may similarly set the system up next to the bench. As used herein, the term "sidelines" thus refers to a location adjacent a sporting field such as a football field, hockey rink, etc. As noted above, the air delivery apparatus 10 may be used to deliver treated air to firefighters and the like, as well. The term sidelines thus by analogy refers to the locations where the air delivery apparatus may be used to deliver treated air to any user. With American football players, some or all of the offensive team members may be connected to the air delivery apparatus on the sideline while the defensive team is on the field, and vice versa.

Turning now to FIGS. 9 through 12, a second preferred ventilation system 100' is disclosed. The ventilation system 100' with which the air delivery apparatus 10 described above may be used is described. Although the ventilation system 100' described herein and shown in FIGS. 9 through 12 is embodied in a garment such as a T-shirt 150, it is to be understood that the ventilation system may also be incorporated with or in other items such as, for example, football helmets, firefighter's headgear, pants, jackets, sports equipment, shoes, gloves, blankets, and any other item that may be used by an individual to modify or regulate the individual's body temperature.

Figure 9:
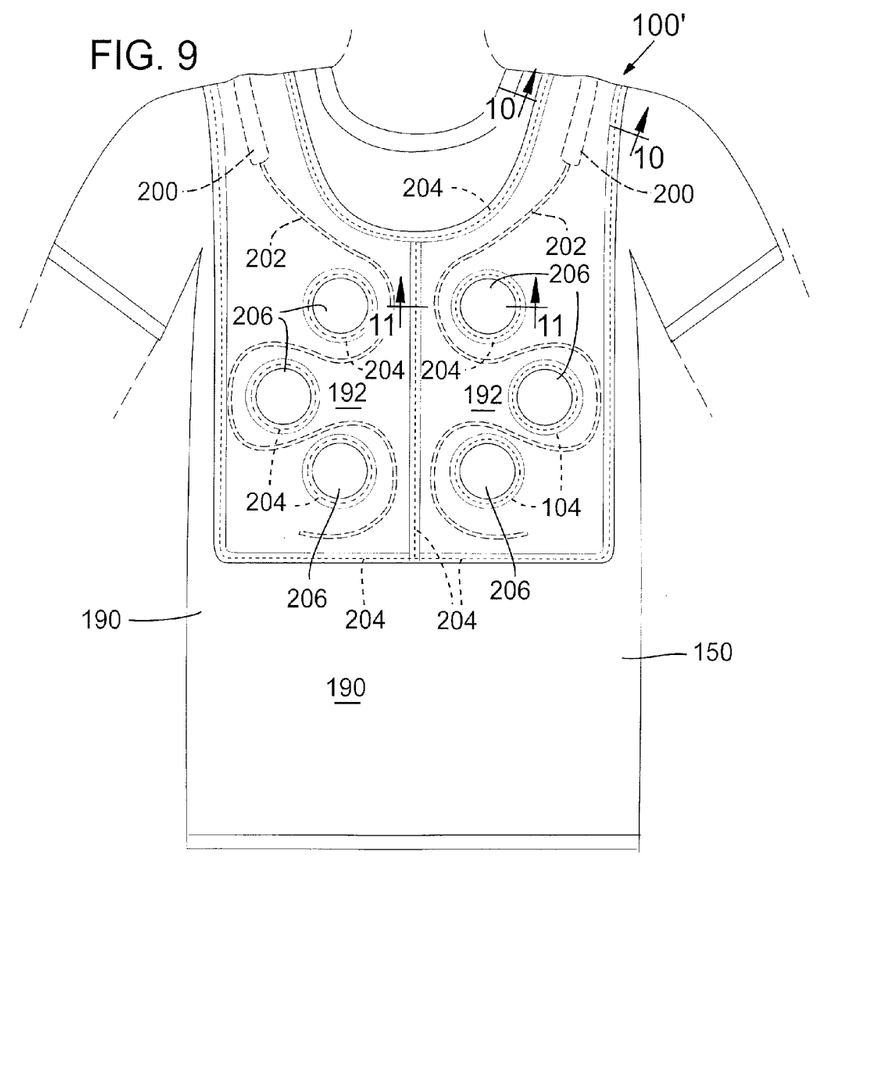
FIG. 9 is a front view a second preferred embodiment ventilation system in this case a ventilation garment having a channels therein that are prevented from collapsing with shoulder support 200 and flexible channel supports 202 imbedded within the channels.
Figure 12:
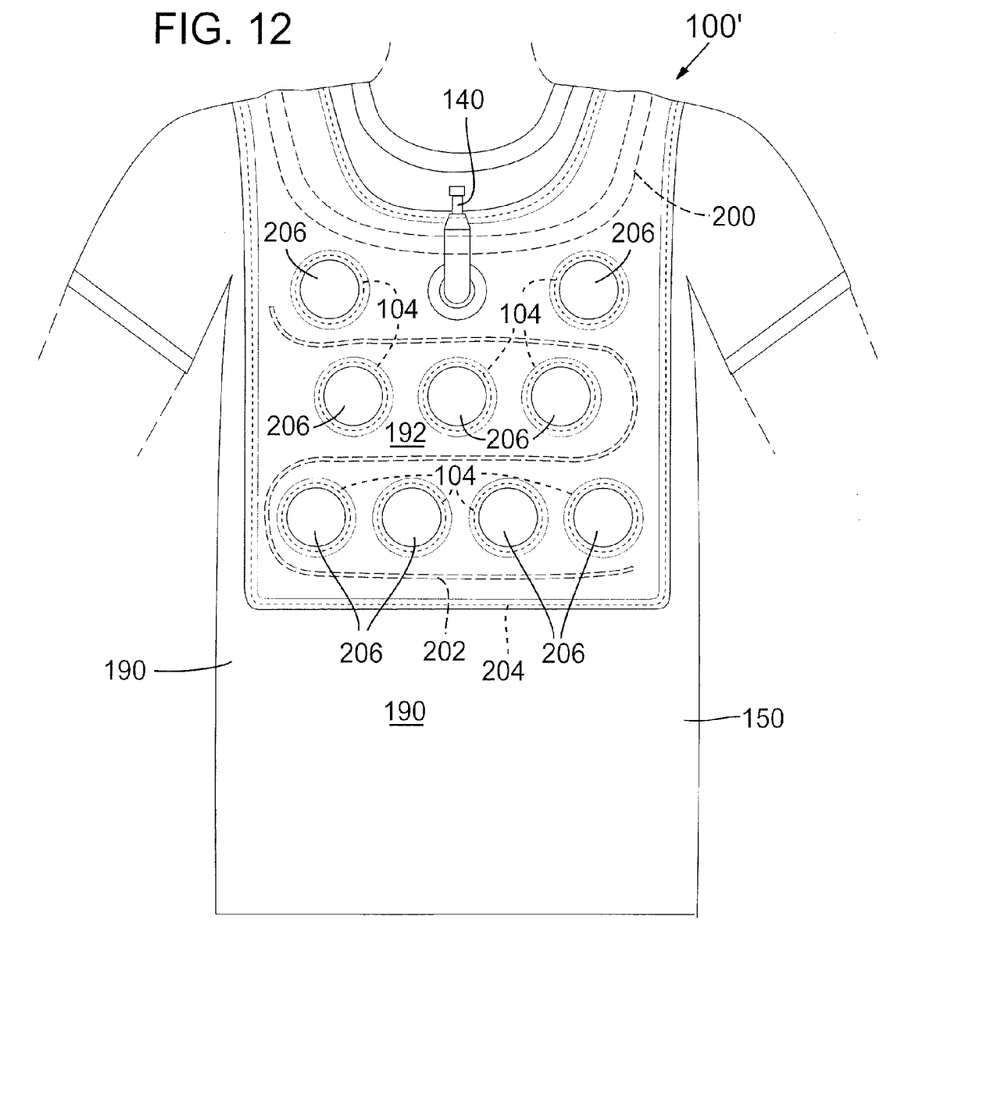
FIG. 12 is a back view of the second preferred embodiment ventilation system of FIG. 9.

With reference to FIGS. 9 and 12, a ventilation system 100' that is designed for incorporation into a T-shirt includes an inner layer 190 and an outer layer 192. Inner layer 190 is preferably a fabric material having microporous structure that has holes of a size that allow air to diffuse through the layer.

The outer layer 192 is preferably a fabric material that is impermeable to air, such as fabric coated with a plastic material. The two layers 190, 192 are sandwiched together atop one another and then sealed along seams 204 such that a continuous pneumatic air chamber is defined therebetween. The air chamber is operatively connected through an air hose 140 to a source of air, such as the air delivery apparatus 10 as previously described herein.

Preferably, portions of the outer layer 192 are pneumatically sealed to the inner layer 190 as best shown in FIGS. 9 and 12 so as to define a plurality of holes 206 in the outer layer 192. These holes 206 allow heat and perspiration from the wearer to escape through the porous inner layer 190 within the holes 206 through the holes 206 in the outer layer 192 to the ambient environment.

Figure 10:
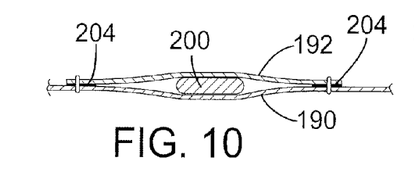
FIG. 10 is a cross sectional view taken along the line 10-10 of FIG. 9.

Preferably an elongate shoulder support 200 and flexible channel supports 202 are interspersed within the chamber as shown so as to prevent the outer and inner layers from collapsing together and help maintain airflow through the chamber during use as best shown in FIG. 10. More preferably, the elongate shoulder support is formed of a flexible, porous, mesh structure, such as a compressed loosely-woven nylon tube or the like, and positioned so as to extend over each shoulder of the wearer and along the upper back as shown. This positioning prevents the upper and lower layers from compressing together at the shoulders, thereby allowing air to freely flow from the air hose 140 at the back of the garment, over the shoulders, to the front of the garment.

Figure 11:
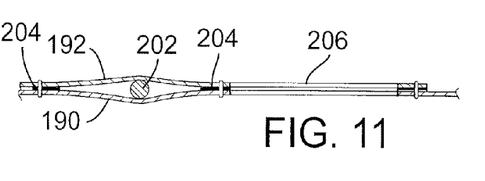
FIG. 11 is a cross sectional view taken along line 11-11 of FIG. 9.

The flexible channel supports 202 are preferably elongate chords that serpentine through the chamber around the holes 206 so as to maintain the inner and outer walls spaced apart from each other as best shown in FIG. 11. More preferably, one distal end of each front-mounted flexible channel support 202 is operably secured to one of the distal ends of the shoulder support 200 as shown.

A separate flexible channel support 202 is preferably provided within the chamber defining the back of the garment as shown in FIG. 12. This prevents the chamber in the back of the garment from collapsing during use.

It will be appreciated that the seams 204 joining the inner layer 190 to the outer layer 192 to define the air chamber therein may be formed with glue applied between the inner and outer layers 190, 192, or may be formed by welding the inner and outer layers 190, 192 together such as with radio frequency welding. Preferably the two layers are also stitched together near the seams 204.

The air chamber and seams around the holes 206 define channels for cooling air to flow from the air hose 140 though the channels through the inner layer. Air is introduced to ventilation system 100 through air hose 140 and flows through channels. When the ventilation system is incorporated into a T-shirt 150, the air channels extend over the front and back portions of the garment so that air flows over the user's back, shoulders and chest. The elongate shoulder support 200 and flexible channel supports 202 sandwich between the inner and outer layers within the chamber prevent the layers from collapsing together thereby maintain air flow within the chamber.

In order to encourage air flow throughout the chamber, the areas where air flow is to be encourage can include more or larger air holes whereas areas where less air flow is desired can include fewer or smaller air holes. For example, the areas around the air tube 140 can include fewer air holes, where areas further away from the air tube can include more air holes to ensure cooling air is widely dispersed throughout the entire garment.

The second preferred ventilation system 100' operates substantially similar to that of the first preferred ventilation system 100 as previously described.

While the present invention has been described in terms of a preferred embodiment, it will be appreciated by one of ordinary skill that the spirit and scope of the invention is not limited to those embodiments, but extend to the various modifications and equivalents as defined in the appended claims.

What is claimed is:

1. An air delivery apparatus, comprising:
a garment that is operable to be worn by an individual, said garment comprising as flexible air permeable fabric inner layer, a flexible air impermeable fabric outer layer, and an intermediate layer that is layered between the inner and outer layers, the intermediate layer having an inner side that abuts and attaches to the inner layer and an outer side that abuts and attaches to the outer layer, a thickness direction being defined between the inner side and the outer side and a span direction being defined perpendicular to the thickness direction, the intermediate layer including an intermediate channel that extends in the thickness direction from the inner side to the outer side, the intermediate channel also extending in the span direction across the garment, wherein the inner and outer layers lie over the intermediate channel such that the inner layer, the outer layer, and the intermediate layer cooperate to define at least one air channel in the garment, wherein said garment also includes a first hole extending through the inner layer and a second hole extending through the outer layer, the first and second holes at least partially overlapping each other to facilitate heat transfer through the first and second holes;
an air compressor;
an air reservoir fluidly connected to the air compressor; and
an air distribution module fluidly connected to the air reservoir and capable of simultaneously delivering air to a plurality of said garments,
wherein the intermediate channel branches off into a plurality of fluidly connected branches of the intermediate channel, and wherein the intermediate layer includes a middle portion that is disposed between the plurality of fluidly connected branches in the span direction, the first hole and the second hole lying over the middle portion of the intermediate layer in the span direction.

2. The air delivery apparatus according to claim 1, wherein said garment includes a fitting for selective connection of the garment to the air distribution module.

3. The air delivery apparatus according to claim 2, wherein the garment is an athletic garment for participating in an athletic event.

4. The air delivery apparatus according to claim 1, wherein the air distribution module is further defined by a main it delivery hose connected to an air dryer and plural branch hoses, each branch hose capable of connection to the plurality of said garments.

5. The air delivery apparatus according to claim 1, further including an air dryer fluidly connected to the air reservoir between the it reservoir and the air distribution module.

6. The air delivery apparatus according to claim 5, having a pressure control valve in a main air delivery hose.

7. The air delivery apparatus according to claim 5, further including an air refrigerator between the air dryer and the air distribution module.

8. The air delivery apparatus according to claim 5, further including an air heater between the air dryer and the air distribution module.

9. The air delivery apparatus according to claim 5, further including an air refrigerator and an air heater between the air dryer and the air distribution module.

10. The air delivery apparatus according to claim 5, wherein the air dryer is operable to dry air delivered to the air distribution module to a relative humidity of less than 50%.

11. The air delivery apparatus according to claim 5, wherein the air compressor is mechanically connected to the air reservoir and the air reservoir is mechanically connected to the air dryer.

12. The air delivery apparatus according to claim 1, wherein the air compressor is an electric rotary vane compressor.

13. The air delivery apparatus according to claim 5, further including a channel support between said air permeable fabric inner layer and said air impermeable fabric outer layer of said garment.

14. The air delivery apparatus according to claim 13, wherein said channel support is formed of a porous mesh structure.

15. The air delivery apparatus according to claim 13, wherein said channel support is an elongate chord.

16. The air delivery apparatus according to claim 1, wherein the intermediate layer includes a third hole, the first, second, and third holes at least partially overlapping each other to facilitate heat transfer through the first, second, and third holes.

17. The air delivery apparatus according to claim 1, wherein the inner layer includes a plurality of pores, and wherein the first and second holes are each wider than each of the plurality of pores.

18. An air delivery apparatus, comprising:
a plurality of garments, at least one of the plurality of garments including a flexible air permeable fabric inner layer with an interior surface, a flexible air impermeable fabric outer layer with an interior surface, and an intermediate layer that is layered between the inner and outer layers, the intermediate layer having an inner side that abuts and attaches to the interior surface of the inner layer and an outer side that abuts and attaches to the interior surface of the outer layer, a thickness direction being defined between the inner side and the outer side and a span direction being defined perpendicular to the thickness direction, the intermediate layer including an intermediate channel that extends in the thickness direction from the inner side to the outer side, the intermediate channel also extending in the span direction across the garment, wherein the inner and outer layers lie over the intermediate channel such that the interior surface of the inner layer, the interior surface of the outer layer, and the intermediate layer cooperate to define at least one air channel in the garment;
an air compressor;
an air reservoir fluidly connected to the air compressor; and
an air distribution module fluidly connected to the air reservoir and fluidly connected directly to the air channel, the air distribution module capable of simultaneously delivering air to the plurality of said garments, the delivered air flowing within the air channel;
wherein the at least one of the plurality of garments further includes a channel support disposed within the channel between said air permeable fabric inner layer and said air impermeable fabric outer layer of the at least one of the plurality of garments, the channel support including an outer surface the channel support limiting compression of the inner and outer layers together to maintain flow of air within the air channel over the outer surface of the channel support; and
wherein the intermediate channel branches off into a plurality of fluidly connected branches of the intermediate channel, wherein said at least one of said plurality of garments also includes a first hole extending through the inner layer and a second hole extending through the outer layer, the first and second holes at least partially overlapping each other to facilitate heat transfer through the first and second holes, wherein the intermediate layer includes a middle portion that is disposed between the plurality of fluidly connected branches in the span direction, the first hole and the second hole lying over the middle portion of the intermediate layer in the span direction.

* * * * *